United States Patent
Kapit et al.

(10) Patent No.: US 12,332,169 B2
(45) Date of Patent: Jun. 17, 2025

(54) DISSOLVED GAS SENSING SYSTEM AND METHOD

(71) Applicant: WOODS HOLE OCEANOGRAPHIC INSTITUTION, Woods Hole, MA (US)

(72) Inventors: Jason Kapit, Woods Hole, MA (US); Anna Michel, Woods Hole, MA (US)

(73) Assignee: Woods Hole Oceanographic Institution, Woods Hole, MA (US)

( * ) Notice: Subject to any disclaimer, the term of this patent is extended or adjusted under 35 U.S.C. 154(b) by 89 days.

(21) Appl. No.: 18/009,294

(22) PCT Filed: Jan. 14, 2022

(86) PCT No.: PCT/US2022/012500
§ 371 (c)(1),
(2) Date: Dec. 8, 2022

(87) PCT Pub. No.: WO2022/155460
PCT Pub. Date: Jul. 21, 2022

(65) Prior Publication Data
US 2023/0221246 A1    Jul. 13, 2023

Related U.S. Application Data

(60) Provisional application No. 63/137,942, filed on Jan. 15, 2021.

(51) Int. Cl.
| | | |
|---|---|---|
| *G01N 21/3504* | (2014.01) | |
| *A61B 10/00* | (2006.01) | |
| *G01N 21/359* | (2014.01) | |

(52) U.S. Cl.
CPC ....... *G01N 21/3504* (2013.01); *G01N 21/359* (2013.01); *A61B 2010/0083* (2013.01);
(Continued)

(58) Field of Classification Search
CPC ............. G01N 21/3504; G01N 21/359; G01N 2201/0634; G01N 2201/0636;
(Continued)

(56) References Cited

U.S. PATENT DOCUMENTS

| | | | |
|---|---|---|---|
| 7,385,692 B1 * | 6/2008 | Nguyen | G01J 3/28 356/301 |
| 2008/0024777 A1 | 1/2008 | Wang et al. | |

(Continued)

OTHER PUBLICATIONS

Zamadar, Matibur; Aebisher, David; Greer, Alexander, "Singlet Oxygen Delivery Through the Porous Cap of a Hallow-Core Fiber Optic Device," Oct. 13, 2009, J. Phys. Chem. B, 113, 15803-15806 (Year: 2009).*

(Continued)

*Primary Examiner* — Edwin C Gunberg
*Assistant Examiner* — Richard O Toohey
(74) *Attorney, Agent, or Firm* — Kean Miller LLP; Robert Devin Ricci; Lauren J. Rucinski (57) ABSTRACT

An apparatus and method of use are provided; the apparatus having at least a degasser, a hollow core fiber HCF, an optical mechanism, a detector, and circuitry. The degasser enables gasses to permeate out of a liquid into the degasser interior. The propagator establishes a low-pressure area that helps to pull the gas from the degasser interior into the HCF interior, where the optical mechanism delivers electromagnetic radiation EMR that interacts with the gas. The detector determines EMR absorption, producing output signals which are sent to the circuitry. Circuitry controls the optical mechanism and analyzes the output signals to quantify the concentration of gas in the HCF and in the liquid.

7 Claims, 9 Drawing Sheets

(52) U.S. Cl.
CPC ............... *G01N 2201/0634* (2013.01); *G01N 2201/0636* (2013.01); *G01N 2201/0826* (2013.01)

(58) Field of Classification Search
CPC ......... G01N 2201/0826; G01N 1/2226; G01N 21/39; G01N 21/03; G01N 2021/0346; A61B 2010/0083; G02B 6/02328
See application file for complete search history.

(56) References Cited

U.S. PATENT DOCUMENTS

| | | | | |
|---|---|---|---|---|
| 2013/0319110 | A1* | 12/2013 | Otera | G01N 21/359 |
| | | | | 73/335.01 |
| 2018/0259444 | A1* | 9/2018 | Buijs | B01D 19/0031 |
| 2020/0348275 | A1* | 11/2020 | Mackenzie | G01N 21/6402 |
| 2023/0003653 | A1* | 1/2023 | Alon | H01S 3/302 |

OTHER PUBLICATIONS

"Singlet Oxygen Delivery Throught the Porous Ca of a Hollow-Core Fiber Option Device", J. Phys. Chem. B 2009, 113, 15803-15806, Oct. 20, 2009.

* cited by examiner

FIGURE 9A
GAS CIRCULATION CONFIGURATION degasser membrane configurations

FIGURE 9B
REFLECTED OPTICAL CONFIGURATION

DISSOLVED GAS SENSING SYSTEM AND METHOD

CROSS-REFERENCE TO RELATED APPLICATIONS

This application is a 35 USC § 371 National Stage application of International Application No. PCT/US2022/012500 filed Jan. 14, 2022, now pending; which claims the benefit under 35 USC § 119 (e) to U.S. Application Ser. No. U.S. 63/137,942 filed Jan. 15, 2021. The disclosure of each of the prior applications is considered part of and is incorporated by reference in the disclosure of this application.

STATEMENT REGARDING FEDERALLY SPONSORED RESEARCH OR DEVELOPMENT

The invention was made with United States Government support by Grant No. NA18OAR0110354 from the National Oceanic and Atmospheric Administration (NOAA). The United States Government therefore has certain rights in this invention.

FIELD OF THE INVENTION

This application relates to detecting molecules in a liquid. More specifically, this invention relates to detecting gases dissolved in a liquid or fluid liquid.

BACKGROUND

The measurement of dissolved gas concentrations is important in a wide variety of industrial, environmental, and biomedical applications. Gases in both the gas phase and dissolved in fluids are commonly measured using absorption spectroscopy due to its advantages of high sensitivity and selectivity. However, reaching high sensitivity and low detection limits often requires multi-pass cells or high finesse cavities, which necessitate precision optical and mechanical components that increase size and fabrication complexity. Measuring gases in dissolved form often requires additional components to equilibrate or extract the gas into a headspace prior to analysis. Such sizable components are not ideal for field portable or in situ sensors in which miniaturization is important. Optical cell miniaturization is desirable when only a limited amount of sample gas is available because it decreases the amount of gas required for analysis. This can be the case for finite samples retrieved in the field, when there is only a small amount of liquid available for analysis, or when the sample is in small or hard-to-reach places.

Therefore, a desired solution is a sensor capable of operating in one or more embodiments, with a small gas inlet, a small optical cell, and/or micro-scale sample gas volumes. These enable improved portability, in situ use, and lower cost. Embodiments of sensors are provided herein to meet one or more of these desires.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

An object of the present invention is to provide a sensor apparatus for measuring at least one gas dissolved in a liquid. In one such embodiment of the present invention, the apparatus comprises a degasser with a gas-permeable and liquid impermeable wall connected to a hollow core fiber (HCF) having a first and a second end and a substantially hollow interior. The HCF is gaseously connected to the degasser and is configured to accept into the HCF interior gas from the degasser, and electromagnetic radiation (EMR). The apparatus further comprises an optical mechanism that is capable of emitting EMR and coupled to the HCF, a propagator capable of creating a low-pressure environment, and a detector capable of detecting the amount and various wavelengths of the EMR within, exiting, or after it has exited a HCF interior, and circuitry. The detector is preferably configured to produce output signals that correspond to the detected EMR and transmit those output signals to the circuitry. In some embodiments, the apparatus also has an inlet that gaseously connects the HCF to the degasser. In one or more embodiments, the inlet gaseously connects at the second end of the HCF; in some embodiments, the inlet couples the HCF to the optical mechanism where the EMR is delivered to the inlet before the HCF. In some embodiments, the apparatus also has an optical fiber that is connected to the optical mechanism and to the inlet where the optical fiber delivers the EMR to the inlet from the optical mechanism. In an alternate embodiment, the sensor apparatus may be configured to measure a liquid headspace without use of a membrane barrier.

In a second principle embodiment, the apparatus further comprises a gas-tight detection chamber connected to the propagator and the HCF first end. In some of these cases, the optical mechanism may be located within that detection chamber. In alternate embodiments, the detection mechanism may be located within that detection chamber, and in yet other embodiments, both the optical mechanism and the detection mechanism may be located within the detection chamber. Furthermore, in alternate or related embodiments, the inlet may be connected to the HCF second end, a mirror may be located within the inlet such that the mirror reflects the EMR passing through the inlet, and the detector is located within that detection chamber. Furthermore, in some of these embodiments, a prism may also be located within that detection chamber and configured to redirect EMR coming from the optical mechanism into the HCF interior and/or redirect EMR coming from the HCF interior to the detector.

In one or more embodiments, an apparatus of the present invention is configured to pull or circulate gas within the apparatus to decrease response time. In such an embodiment, the apparatus may further comprise a propagator connected to the degasser, and said propagator is configured to circulate gas through the degasser and HCF interior by establishing a low-pressure area. In some cases, the propagator is attached to a waste stream capable of removing gas from the detection chamber. In some cases, the propagator is connected to the degasser indirectly through a linker (and not directly to the degasser). In other cases, the propagator establishes an initial low-pressure area and then deactivates. In such an embodiment, it may be advantageous that the apparatus be at least substantially gas-tight to make use of the low pressure area. As such, the low-pressure area persists, drawing any gas from the degasser into the HCF.

In some embodiments, the degasser is a capillary tube; in some cases, the degasser is further a branched capillary tube. In other embodiments, the degasser is a disk or thin membrane. The circuitry may also be configured to control the optical mechanism and receive the output signals from the detector.

This application further discloses a method of detecting a gas dissolved in a liquid, the method comprising the steps of (a) providing an apparatus as described above; (b) placing the degasser into a liquid which has at least one dissolved gas therein; (c) diffusing the at least one gas from the liquid into the HCF interior; (d) emitting EMR from the optical mechanism and into the HCF interior; and (e) detecting the EMR with the detector. Some methods may include the additional step of (f) establishing a low-pressure area with the propagator. More robust methods may also include the steps of (g) producing output signals by the detector, the output signals corresponding to the detected EMR and (h) sending the output signals to the circuitry. Some methods further include the step of (i) controlling the optical mechanism with the circuitry. In one or more embodiments, the methods may include an apparatus that also has a detection chamber connected to the propagator and the HCF first end, where the optical mechanism is located within the detection chamber. Some of these methods include an apparatus that also has an inlet connected to the degasser and the HCF second end and a mirror within the inlet. The mirror is capable of reflecting the EMR and the detector is also within the detection chamber. In some of these methods, the apparatus also has a prism within the detection chamber that redirects EMR from the optical mechanism into the HCF interior and redirects EMR from the HCF interior to the detector. Some of these methods further include the step of directing EMR emitted from the optical mechanism into the HCF interior by the prism and directing EMR from the HCF interior to the optical mechanism by the prism. Some of these methods further comprise the step of (j) reflecting the EMR exiting the HCF second end, with the mirror, back into the HCF second end.

In some instances, the degasser is introduced to a liquid within a sample container. In related embodiments, such as with the use of a field kit, the degasser is introduced to a liquid that is a larger body of liquid. In some cases of the first method circumstance, the degasser is introduced to a liquid that is a bodily fluid.

In some embodiments, the method may include the step of (k) placing the degasser into a patient's body or otherwise placing the degasser into communication with a body. The method may further include the steps of attaching a needle and introducer sheath to the degasser; inserting the needle into a patient's body, moving the introducer sheath into the patient's body; and moving the degasser through the needle and introducer sheath into the patient's body.

In some cases of the first method circumstance, the apparatus is placed into a submersible housing, the housing having an opening for the degasser, where the degasser and the opening form a liquid tight seal, preventing the liquid from entering the housing interior. And the apparatus, inside its submersible housing, is placed into the liquid.

In one or more embodiments, the apparatus may be configured to operate on a lab bench. In alternate embodiments, the apparatus may be designed in a space saving configuration. In a related embodiment, the apparatus may be built into a carry compartment to allow for field use. In such an embodiment, the components may be ruggedized.

BRIEF DESCRIPTION OF THE DRAWINGS

In what follows, preferred embodiments of the invention are explained in more detail with reference to the drawings, in which.

DEFINITIONS

The term "gaseously connected" as used herein refers to at least two components that are connected, either directly or indirectly through another component, such that a gas may move from one component to the next or otherwise between the two components.

DETAILED DESCRIPTION

Overview

Figure 1A:
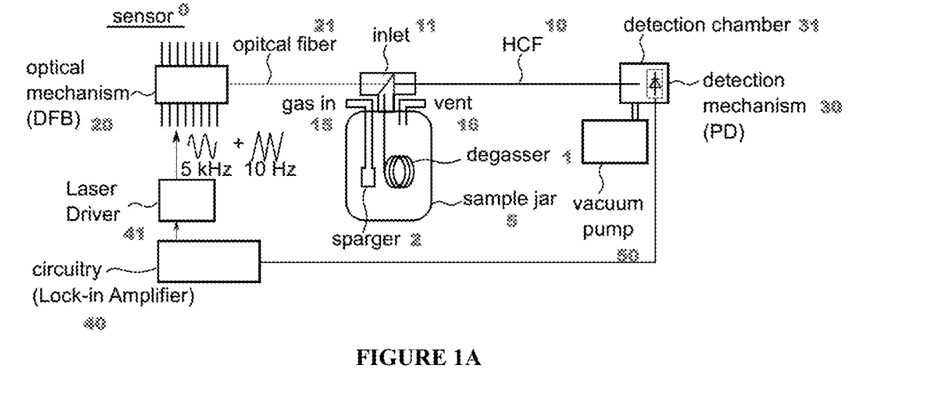
FIGS. 1A and 1B illustrates one embodiment, FIG. 1A depicting the dissolved gas sensing, and FIG. 1B depicting a gas phase calibration.
Figure 1B:
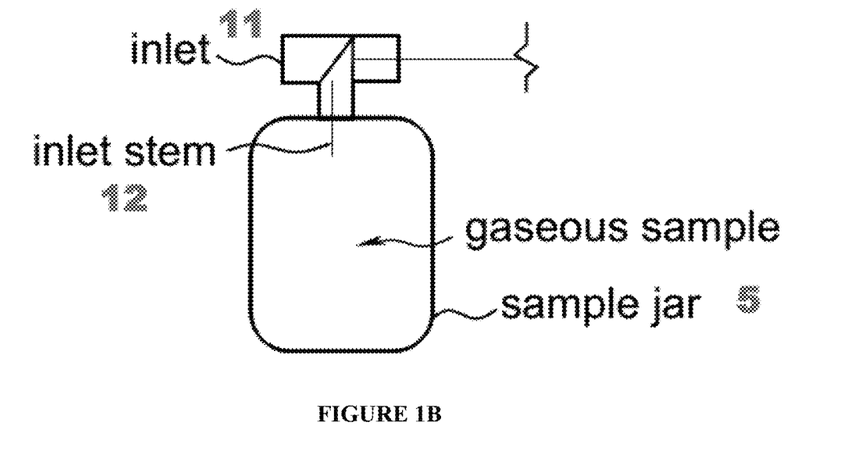

Turning to FIGS. 1A and 1B, the present disclosure describes, in one embodiment, a gas sensing apparatus (referred herein as the sensor) 0 having an inlet interconnecting (i) a degasser 1, (ii) a hollow core fiber (HCF) 10, and (iii) an optical mechanism 20; a detection mechanism 30 and circuitry 40, as illustrated in FIG. 1. The degasser 1 is a gas permeable membrane or other suitable mechanism that, when immersed in a fluid, enables gas to dissolve out of the fluid and into the interior of the degasser. The inlet 11 connects the degasser to the HCF 10. The HCF 10 and the inlet 11 are also coupled to the optical mechanism, enabling the delivery of electromagnetic radiation (e.g., laser light) through the HCF interior and to the detection mechanism. This invention enables a compact dissolved gas sensor that needs only microscopic gas volumes, as well as providing sensors in different embodiments with different path lengths, while maintaining a small form factor by utilizing a HCF.

Figure 1C:
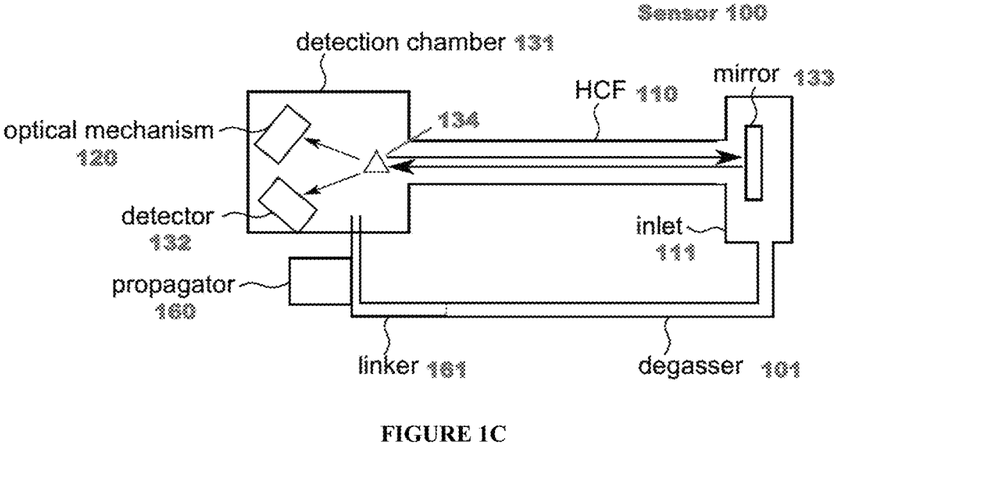
FIG. 1C illustrates a second embodiment according to the present disclosure.

Turning to FIG. 1C, the present disclosure includes additional embodiments including a gas sensor 100 having a HCF 110 connected to an inlet 111 and a detection chamber 131, a gas-permeable degasser 101 connected to the inlet 111 that receives gasses as they diffuse out of a liquid, the gas entering the HCF 110 from the inlet 111. The detection chamber 131 is located at the opposite end of the HCF 110 as the inlet 111 and has within it an optical mechanism 130 and a detector 132, while the inlet 111 has within it a mirror 133. The optical mechanism 130 emits electromagnetic radiation (e.g., light), a prism mechanism 134 directs the light into the HCF 110, the light is reflected at the mirror 133 and is directed back into the HCF 110. At the prism mechanism 134, the light is directed towards the detector 132. In some cases, a propagator 160 establishes a low-pressure area in the detection chamber 131, pulling gas from the degasser 101 into the HCF 110. In additional cases, the propagator 160 is further attached to a linker 161 connected to the degasser 101, and the propagator 160 enables the circulation of gas from the degasser 101 to the HCF 110, then to the detection chamber 131, to the linker 161 and back to the degasser 101.

In the currently preferred embodiment, the HCF is an anti-resonant hollow core fiber (AR-HCF). Furthermore, in the embodiment depicted in FIG. 1A, 2f wavelength modulation spectroscopy (WMS) is used to measure dissolved gases in liquids. One having skill in the art would recognize that alternate embodiments exist, and indeed, some illustrative embodiments are provided herein. For illustrative purposes, the sensor may employ a novel gas-permeable polymer degasser membrane and inlet such as the embodiment set forth in FIGS. 9C and 9D (showing degasser membranes 480 and 580 respectively). One novel aspect of this innovation is that embodiments may be configured to operate on a small amount of gas to fill the chamber, allowing for an embodiment with a small gas-permeable membrane.

Degasser

The present disclosure provides for a mechanism for extracting gas dissolved in a liquid into a gas phase and into the HCF 10, referred herein as the degasser 1. The degasser may be any suitable gas-permeable and liquid-impermeable mechanism as known in the art. When immersed in a liquid, the degasser enables gases dissolved in a liquid to diffuse out of the liquid and into the degasser interior, while blocking the entry of the liquid itself. The degasser 1 is coupled to the HCF 10 by the inlet 11, such that gas in the degasser 10 interior may move into the HCF 10 interior. In some embodiments the degasser is also connected to a linker 161. The linker may be used to allow for the circulation of gas through the sensor (For example, sensor 100 in Figure C depicts such a linker).

Figure 9A:
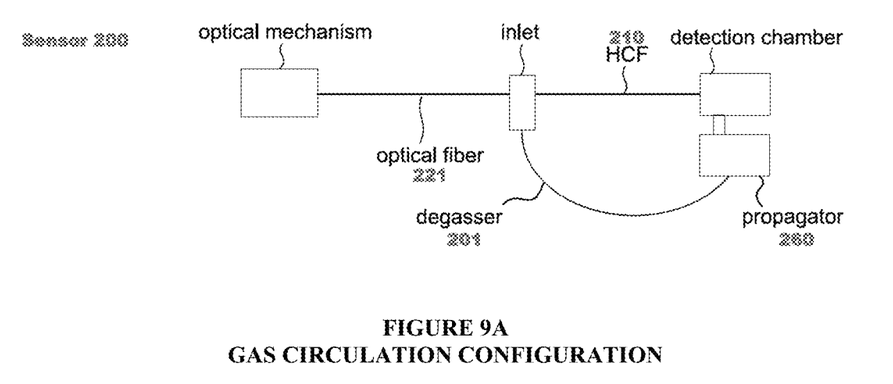
FIGS. 9A-9F illustrate six additional embodiments of the present invention.
Figure 9B:
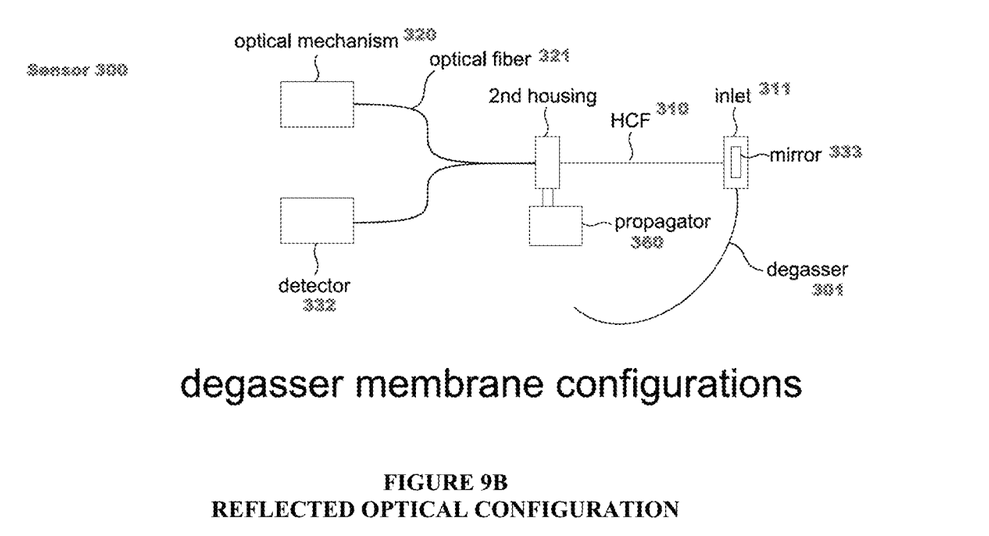
Figure 9C:
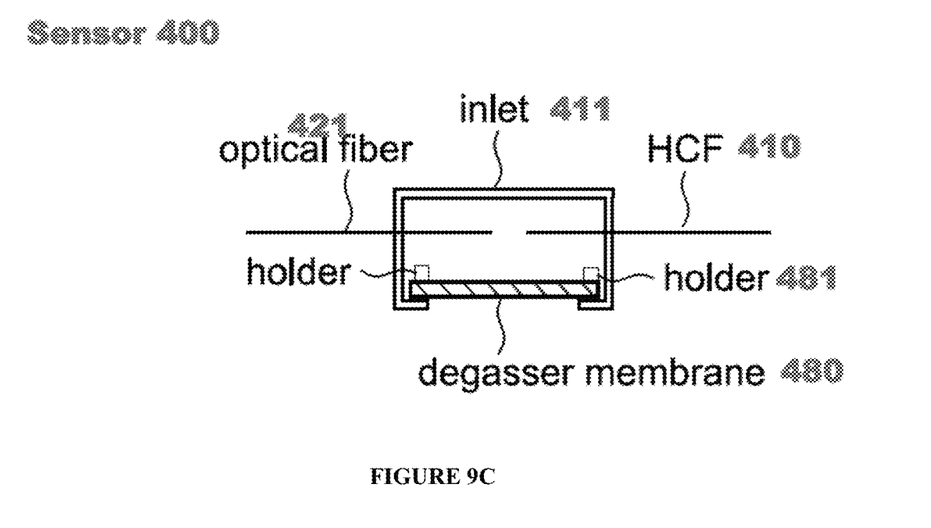
Figure 9D:
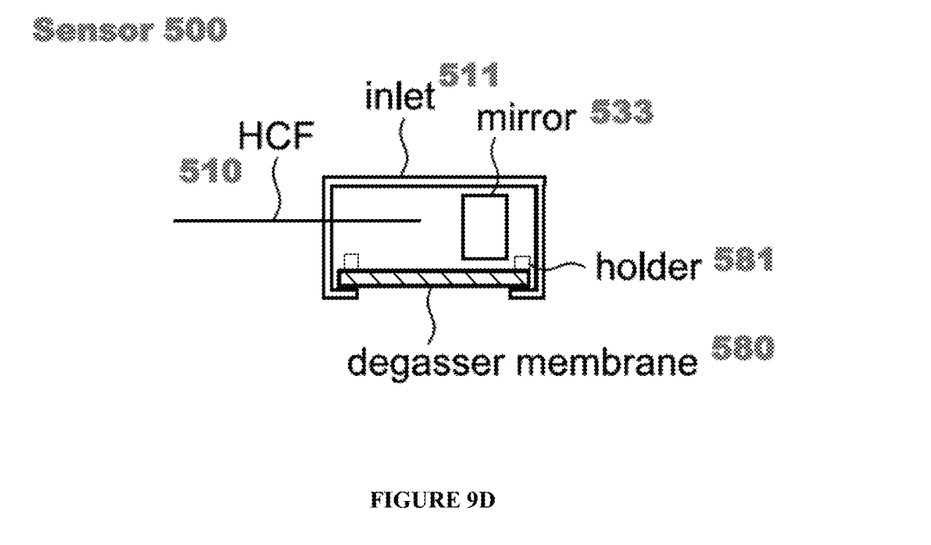

The degasser may be of any suitable geometry. In some embodiments the degasser may comprise one or more capillary tubes. In such an embodiment, the degasser may be a single tube, multiple tubes, or branching tubes. In other embodiments, the degasser is a disk or a sphere of gas-permeable material. In other embodiments, the degasser is a combination of geometries (e.g., tubes and disks). In the currently preferred embodiment, the degasser 1 comprises a Teflon AF polymer capillary. In another embodiment, the degasser comprises a silicone/polydimethylsiloxane (PDMS) capillary. In some embodiments, the capillary is a mixture of chemical constituents. The exact physical dimensions including width and length may vary depending on the embodiment. In some embodiments, such the one depicted in FIG. 1A, the degasser 1 is capped or otherwise terminates. In other embodiments, such as the one depicted in FIG. 1C, the degasser 101 is gaseously connected to another component, for example a linker 161. In additional embodiments, the degasser may be connected to the detection chamber or to the propagator. In still other embodiments, such as the embodiment of Sensor 200 in FIG. 9A, the degasser is connected to the inlet 211 and the propagator 260 FIG. 9, also enabling gas circulation in these embodiments. Turning briefly to FIGS. 9C and 9D, embodiments are shown wherein the degasser comprises a gas-permeable membrane 480 and/or 580. These membrane degassers may be in a separate structure or incorporated into the inlet.

Hollow Core Fiber

The present disclosure provides for a component in which detection of an analyte within a gas occurs, referred herein as the hollow core fiber or HCF 10. The HCF 10 is gaseously connected to the degasser 1 by the inlet 11, enabling the gas exiting the degasser to enter one end of the HCF. Depending on the embodiment, gas may exit the opposite end of the HCF either at the detection mechanism or inside of an optional detection chamber. For example, in Sensor 1 depicted in FIGS. 1A and 1B, gas may pass from the degasser 1 through the inlet, enter one end of the HCF, and pass into the detection chamber 31, wherein detection mechanism 30 is located. In Sensor 100 depicted in FIG. 1C, gas may pass from the degasser 101 through the inlet 111, enter one end of the HCF 110, and pass into the optical detection chamber 131, wherein optical mechanism 120 and detector 132 is located. As discussed further herein, sensor 100 further employs components (e.g., a mirror 133) to reflect light back through the HCF before it enters the detection chamber. The HCF may be any suitable hollow, gas-impermeable structure as known in the art. The HCF most typically couples to the optical mechanism such that the optical mechanism's output, typically electromagnetic radiation (e.g., laser light), enters the gas-fillable volume HCF interior. The HCF must further couple to the detection mechanism such that the detection mechanism detects the electromagnetic radiation exiting the HCF and any absorptions thereof.

Different types of fibers or hollow structures may be used for the HCF. For example, the HCF may be selected based on the type of analyte the sensor is intended to measure. The operating range of different fibers differ, enabling different embodiments to detect different analytes. In the currently preferred embodiment, the HCF comprises an anti-resonant hollow core fiber (AR-HCF), with an operating range of 1350 nm to 1850 nm, enabling detection of several analytes. Additionally, embodiments may include multiple HCFs, multiple optical mechanisms, or both multiple HCFs and multiple optical mechanisms. Some embodiments of the present invention may have more than one HCF (of a similar or a differing type), where each HCF gaseously attaches to the degasser at the inlet and are all coupled to one or more detector and/or optical mechanisms. In some embodiments, multiple optical mechanisms emit EMR into a single HCF. In other embodiments, multiple optical mechanisms emit into multiple HCFs, and one detector mechanism receives the EMR from the multiple optical mechanisms. In some embodiments, multiple detector mechanisms receive the EMR from the one or more optical mechanisms. In other embodiments one optical mechanism emits EMR into multiple HCFs with one or more detectors. Preferably, each HCF would have a dedicated detection mechanism, and each HCF would have different properties (e.g., different lengths for different sensitivities), enabling sensing of multiple analytes in one apparatus.

The HCF may be any suitable fiber as known in the art, including but not limited to hollow core photonic crystal fibers, anti-resonant hollow core fibers, and dielectric hollow core waveguides. A key advantage of the present innovation is the use of these fibers to allow for longer interaction time for a smaller amount of sample than sensors known in the art. These fibers have the advantage of providing long light and gas interaction lengths with extraordinarily small sample volumes; for example, requiring only 2 to 200 nanoliters of gas to fill a 1-meter-long fiber. Thus, as an example, extracting enough atmosphere-equilibrated gas from water to fill the fiber would require degassing only 0.09 to 9 microliters (µL) of water. These characteristics are particularly advantageous for membrane-based dissolved gas sensors due to the slow nature of gas diffusion across the membrane. Thus, minimizing the amount of gas required for analysis can be key in both miniaturizing the size of the gas inlet as well as decreasing the sensor response time. This may have further benefits when sample sizes are small, including without limitation, in the medical setting. In some embodiments, such as the embodiment depicted in FIG. 9F the HCF 710 further has micro holes or micro channels formed into its walls, referred herein as micro-openings 714. These micro-openings enable faster gas entry and exit into and out of the HCF. HCF having micro-openings may be incorporated into practically any other embodiment described elsewhere herein. One method of making micro-openings in a HCF is described by Hoo et. al, "Fast Response Microstructured Optical Fiber Methane Sensor With Multiple Side-Openings" in IEEE Photonics Technology Letters, Vol. 22, Issue 5, published Mar. 1, 2010, incorporated by reference in its entirety herein. In one embodiment, an HCF with micro-openings may be placed directly into a degasser capillary. FIG. 9F illustrates a degasser in cross-section with a HCF containing micro-openings (depicted as a tube with small black circles) interior to the degasser.

In addition, the HCF choice enables the sensor to use different wavelengths of electromagnetic radiation. Typical embodiments utilize wavelengths in the ultraviolet, visible, near infrared, mid infrared, and infrared spectrums. An appropriate optical mechanism is paired with the desired HCF to achieve optimal analyte gas sensing, as well as the optimal path length and sensitivity level.

In effect, the use of the HCF allows for a longer interaction of the sample even when provided in lower volumes. It further allows the system to be configured in different ways than sensors known in the art. For example, embodiments with smaller footprints are much more achievable. Likewise, the need for a lot of gas may be a limiting factor in traditional sensors—in terms of collection, time for analysis, structure of the system, and application. For example, sensors that require too much sample cannot be readily used to detect gasses in a living body.

Inlet

The present disclosure provides for a mechanism to couple the optical mechanism 20 (and optical fiber 21, if present) and degasser 1 to the HCF 10, referred herein as the inlet 11. The inlet enables the optical mechanism's electromagnetic radiation to enter the HCF, as well as gaseously connecting the degasser to the HCF, enabling gas to move to or between the degasser and the HCF. In some embodiments, an optical fiber 21 connects the optical mechanism 20 to the inlet 11. The optical fiber 21 is coupled such that electromagnetic radiation is not blocked or substantially obscured as it passes through the inlet 11 and into the HCF 10. The inlet 11 may be any suitable mechanism as known in the art. In the currently preferred embodiment, the inlet 11 that comprises a FC/APC (ceramic ferrules/angled physical contact) connector for the optical fiber 21 and an FC/PC (ceramic ferrules/physical contact) connector for the HCF 10. Typically, in embodiments with an optical fiber, a small gap (e.g., <100 micrometer) exists between the optical fiber and the HCF through which gas enters the HCF from the degasser. Preferably, the inlet is constructed to minimize the gas volume inside the inlet, further enabling small sample sizes.

Figure 9E:
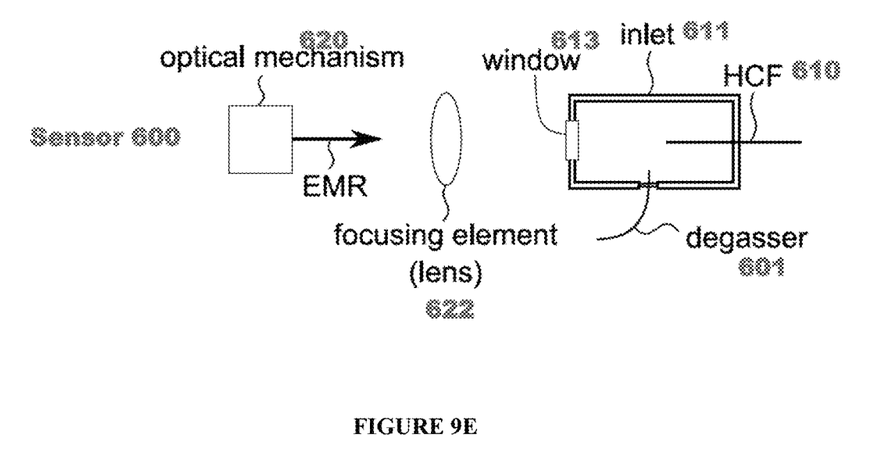
Figure 9F:
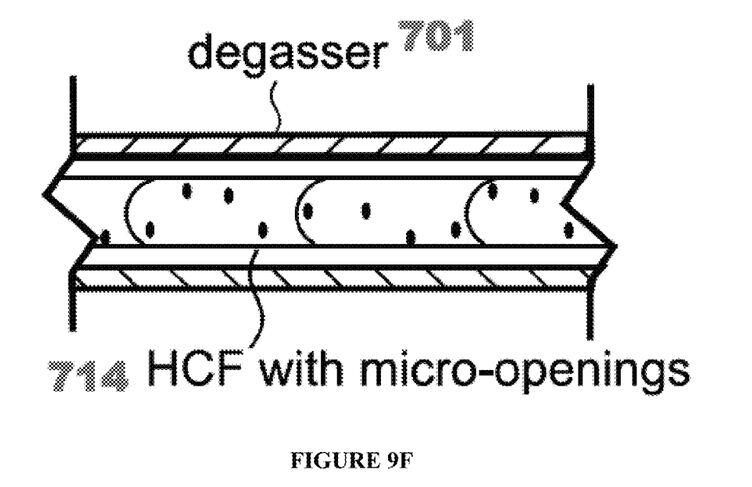

In some embodiments, as illustrated in FIG. 9E, the inlet further comprises an optical window 613. The optical window allows the EMR to enter the inlet 611 from the optical mechanism 620 (as depicted, this embodiment does not have an optical fiber), while maintaining the gas-tight nature of the inlet. Often these embodiments further comprise a focusing element (e.g., a lens) 622 to focus the EMR into and through the optical window 613.

Analyte Equilibrium

Figure 7A:
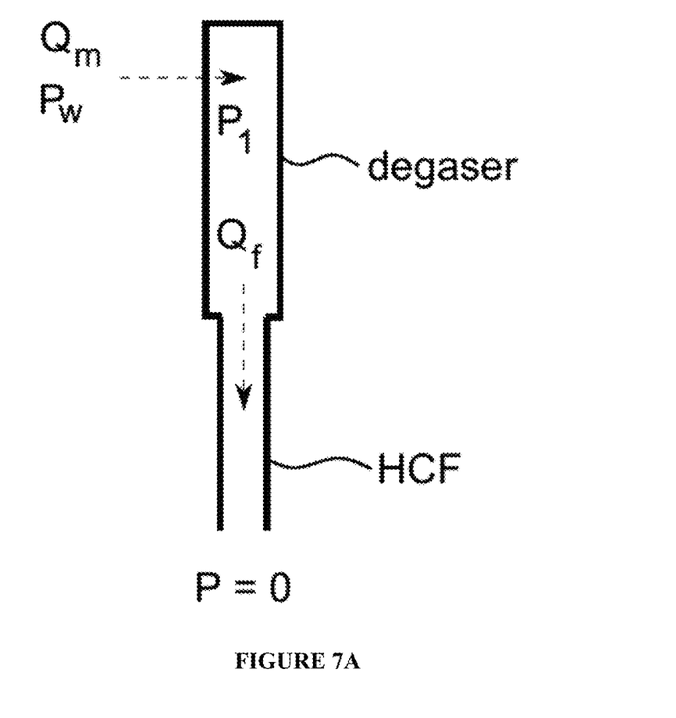
FIG. 7A illustrates a simplified model for determining the gas flux though the degasser and HCF and FIG. 7B is a graphical representation of the gas equilibration model for the exemplary embodiment, here a 1 meter-long tube degasser achieved greater than 90% equilibration between dissolved gas and gas in the inlet interior.

In some embodiments, analyte equilibrium between the liquid, degasser, and hollow core fiber HCF is convenient for robust analyte sensing by the sensor. While analyte equilibrium may be useful for a given embodiment, it is often not necessary and may result in longer response times. For embodiments using analyte equilibrium, the present disclosure provides for optimal properties and calculations to ensure good calibration between dissolved analyte in the solution and analyte inside the degasser. Ideally, analyte gas pressure inside the degasser closely matches the pressure of the dissolved analyte in the sample solution being measured. For one embodiment of a degasser, this can be modelled by assuming the gas flux through the degasser walls, as illustrated in FIG. 7A, due to Darcy's Law is equal to the gas flux through the HCF, where Qm is the gas flux through the degasser due to Darcy's Law, Qf is the gas flux through the HCF due to Hagen-Poiseuille flow, Pw is the dissolved gas pressure in solution, and P1 is the gas pressure inside the degasser inlet and at the connection to the HCF. This gives Darcy's Law in cylindrical coordinates for the degasser as expressed in Math 1.

$$Q_m = \frac{k \cdot 2\pi L_c}{\ln(r_o/r_i)}(P_w - P_1) \qquad \text{Math 1}$$

Additionally, $r_o$, $r_i$ and $L_c$ are the degasser's outer radius, inner radius, and length. $P_w$ is the dissolved gas pressure outside the degasser, P1 is the gas pressure inside the degasser and k is the permeability of gas through the degasser wall, usually expressed in Barrer.

For the HCF dimensions (e.g., 46 µm core and 24 µm cladding tubes) and pressures (e.g., 101 kPa to vacuum) used in the currently preferred embodiment, the Knudsen number is mostly in the hydrodynamic regime. Thus, for simplicity, the flow through the full HCF may be modelled using Hagen-Poiseuille flow, and the gas flux at the HCF inlet, $Q_f$, is expressed using two terms, one for the HCF core and one for the seven cladding tubes, as shown in Math 2, where $P_1$ is the gas pressure at the HCF fiber inlet, $R_{core}$ and $R_{clad}$ are the radius of the HCF fiber core and cladding tubes, $L_f$ is the fiber length, and η is the dynamic viscosity of the gas, taken to be 18 μPa·s.

$$Q_f = \frac{\pi P_1}{16\eta L_f}\left(R_{core}^4 + R_{clad}^4\right) \qquad \text{Math 2}$$

Setting $Q_m = Q_f$ results in Math 3 for $P_1$ and where the rearrangements results in Math 4 & 5.

$$P_1 = \frac{C_m P_w}{C_f + C_m} \qquad \text{Math 3}$$

$$C_m = \frac{k \cdot 2\pi L_c}{\ln(r_o/r_i)} \qquad \text{Math 4}$$

$$C_f = \frac{\pi}{16\eta L_f}\left(R_{core}^4 + 7R_{clad}^4\right) \qquad \text{Math 5}$$

Figure 7B:
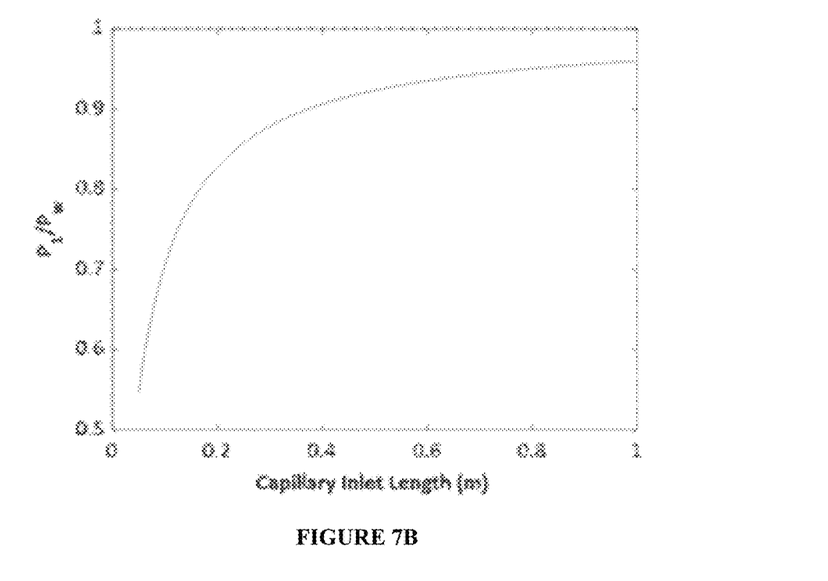

Overall, the main requirement needed to ensure good equilibration on either side of the degasser is for P1 to be close to Pw, which define as P1≥0.9 Pw. FIG. 7B shows the ratio P1/Pw for a given analyte as a function of the length of the degasser for the setup used in the example described herein below. It indicates the degasser length of 1 m was long enough to achieve >90% equilibration, and a degasser as short as 40 cm would have sufficed. Exact calculations for different analytes may change the physical parameters of degasser and HCF, as needed.

Optical Mechanism

The present disclosure provides for a mechanism to emit a detective force for analyte analysis, referred herein as the optical mechanism. The optical mechanism may be any optical-based solution for analyte analysis, most typically a laser-based solution. The optical mechanism emits a detective force, most often electromagnetic radiation (e.g., light at precise wavelengths or wavelength) that is directed into the HCF. In some embodiments, the electromagnetic radiation is first received by the inlet and then delivered to the HCF (see FIG. 1A), in other embodiments the electromagnetic radiation is delivered directly to the HCF (see FIG. 1C). The wavelength of electromagnetic radiation may vary depending on the embodiment; it is within the scope of the present invention for the optical mechanism to produce electromagnetic radiation of 0.20 to 10 μm wavelength, in some cases 15 or 25 μm wavelength.

In the currently preferred embodiment, the optical mechanism 20 is a distributed feedback laser (DFB), for example the Eblana Photonics EP1654-DM-B laser and the optical mechanism is coupled to the inlet 11 by an optical fiber 21. An optical driver 41 (which may be a laser driver) may be attached to the optical mechanism 20 and circuitry 40 and be used to control the wavelength of the electromagnetic radiation, as well as current and temperature tuning.

Optical Mechanism Control

The optical mechanism 20 may be controlled by components described elsewhere herein, typically the optical driver 41 and the circuitry 40. These components modulate or otherwise control current signal delivered to the optical mechanism, enabling efficient analyte detection by the optical mechanism's output (i.e., electromagnetic radiation). Typically, control of the optical mechanism includes controlling the input current and temperature. For example, in the preferred embodiment, the circuitry 40 controls the generation of the small amplitude 5 kHz sine wave laser current modulation signal. And the amplitude of the current modulation waveform may be adjusted and controlled to maximize the magnitude of the 2f signal. The control may then change according to the use of the sensor as needed; for example, a triangle waveform may be added to the optical mechanism modulation for scanning the optical mechanism's center wavelength and observe the 2f signal for the full absorption feature of a given analyte (e.g., scanning across the methane transition at 1650.96 nm; see FIG. 2).

Figure 3:
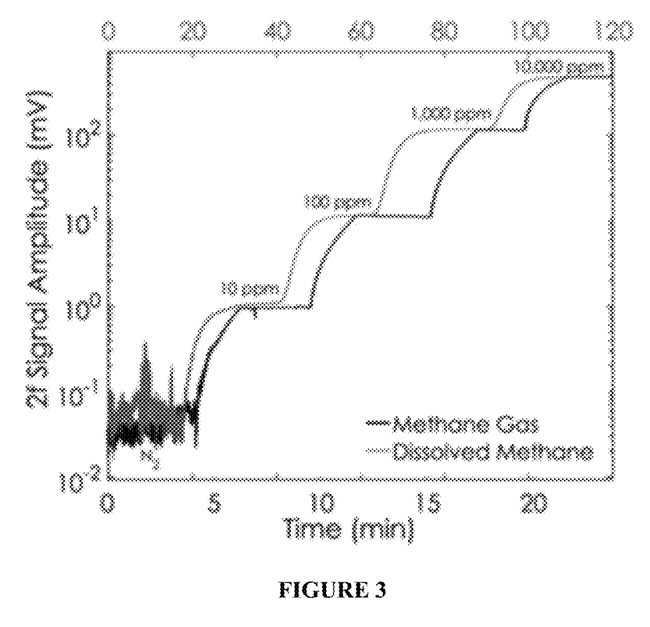
FIG. 3 is a time series of two calibrations of an analyte (here methane) from 0 ppm to 10,000 ppm. The first calibration was obtained by sending methane gas directly into the AR-HCF (dark color). The second calibration was obtained by measuring dissolved gas extracted by the degasser membrane inlet (light color). Note the longer time scale for the dissolved gas calibration (top blue axes, also in minutes).

After, or in place of, scanning, control of the optical mechanism may be held (passively or actively) at the analyte transition wavelength (e.g., 1650.96 nm for methane). Further calibration with a gaseous sample (i.e., analyte gas not dissolved in a liquid) could be conducted to choose the best transition wavelength for one or more analytes. Typically, calibration would be conducted with a liquid, dissolved gas sample having a known concentration of dissolved analyte. Often, calibration is conducted by removing the degasser from the sensor, placing a gaseous sample onto the exposed inlet degasser acceptor (typically a small stem), allowing the gas to enter the HCF, and letting the signal to stabilize. Calibration may be conducted at a specific gas concentration (typically measured in parts-per-million, ppm) or over a range of gas concentrations, such as set forth in the chart in FIG. 3.

In other embodiments, optical mechanism control is achieved by utilizing direct absorption spectroscopy. In these embodiments, the wavelength or wavelengths used by the optical mechanism (e.g., a laser) is scanned using a repetitive current or temperature ramp or triangle waveform. Direct absorption spectroscopy therefore measures the absorption of EMR as a function of frequency or wavelength; where the intensity of absorption varies as a function of frequency and this variation is the absorption spectrum analyzed by the circuitry and associated software.

Detection Mechanism

The present disclosure provides for a mechanism to detect the electromagnetic radiation exiting the HCF, referred herein as simply the detector 32. The detector may be any suitable component as known in the art. In the currently preferred embodiment, the detector is a photodiode, which measures the absorption signal resulting from analyte gas absorption of a portion of the electromagnetic radiation occurring inside the HCF 10 interior. The sensed absorption signal is referred herein as the output signal and is sent to the interconnected circuitry 40.

Detection Chamber

The present disclosure provides an optional gas-tight enclosure for surrounding the detector, referred herein as the detection chamber 31. The detection chamber 131 shown in FIG. 1C is most preferably gas-tight (i.e., sealed) and is connected to a propagator 160, which is used to create a pressure differential between the degasser 101 and one end of the HCF 110. Such pressure gradients facilitate rapid filling of the HCF. Gas may escape the detection chamber, through a detection chamber outlet, typically connected to the propagator, a waste stream, or back into a circulation loop with a linker connected to the degasser.

Propagator

The present disclosure provides for a mechanism to move analyte gas between components, referred herein as the propagator 60. The propagator enables an embodiment to quickly move gas from the degasser to the attached HCF where analyte detection occurs. The propagator may be located at any suitable site; however, as shown in FIG. 1C, the propagator 160 is typically located at or in near proximity to the detector chamber 131. In some cases, the gas is then expelled out of the sensor. Gas expulsion may occur at any suitable site. Typically, the expulsion occurs at or in near proximity the detection chamber or at an end of the HCF. In other cases, the propagator circulates the gas though the components, keeping the gas substantially within the HCF or enabling it to exit and reenter the HCF.

In some embodiments, such as sensor 100 illustrated in FIG. 1C, the degasser 101 is connected to a linker 161 in addition to the inlet 111. And the linker 161 is connected to the detection chamber 131 and the propagator 160 circulates the gas from the detection chamber 161 and back into the degasser 101, often by means of creating a low-pressure area at the propagator. In other embodiments, the degasser is connected directly to the propagator. In still other embodiments the degasser is connected directly to the detection chamber. Typically, the propagator establishes a low-pressure area at or near the site of the propagator, and therefore a high-pressure area (relative to the established low-pressure area) is created at the degasser. The different gas pressures enable the movement of gas from the area of high-pressure to area of low-pressure. In some cases, the propagator is connected to the linker and to a waste stream, enabling both gas circulation and removal of at least a portion of the gas in the sensor.

In some embodiments, the propagator is a vacuum pump that establishes a low-pressure area in the detection chamber, creating a pressure differential between inlet and outlet (of the detection chamber), drawing gas into the HCF, and then out through said outlet. The propagator enables a flow of gas through the HCF, significantly decreasing the response time of the sensor to minutes from hours. In one embodiment the response time of the sensor, where analyte gas in the HCF is at equilibrium with the amount of gas dissolved in the liquid, is less than 20 minutes; in additional embodiments the response time is less than 15 minutes, less than 10 minutes, less than 5 minutes. In most embodiments, the propagator requires a power source to achieve analyte gas equilibrium.

In some embodiments, the propagator establishes an initial low pressure area and then deactivates. This function is particularly useful in embodiments where the sensor apparatus is gas-tight (excluding the gas-permeable degasser) and the propagator presents the only gas removal means in the apparatus. Because the sensor is gas-tight, the established low pressure area persists, drawing any gas in the degasser into the detection chamber and HCF.

Circuitry

The present disclosure provides for a mechanism to control the optical mechanism function as well as record detection mechanism output, referred herein as the circuitry 40. Typically, the same component does both functions; however, it is within the scope of this disclosure for a first circuitry component or set of components to control the optical mechanism and for a second circuitry component or set of components to record the detection mechanism operation. In some embodiments the circuitry also comprises a processor or other digital control mechanism (e.g., for illustrative purposes, a single board computer). Typically, a processor within the sensor apparatus may be any suitable processor as known in the art. The term "circuitry" as used herein also encompasses associated machine readable code (i.e., software, firmware) that enables the circuitry to perform its actions and to covert the signal from the detector into useful information, for example, an analyte concentration. In the currently preferred embodiment, the circuitry comprises a laser driver 41 and a lock-in amplifier 42. The lock-in amplifier is operatively connected to both the optical (laser) driver 41 and the detection mechanism 30. The optical driver is connected to the optical mechanism (e.g., a laser) 20. The lock-in amplifier 42 generates, or causes to be generated, current modulation signal, as well as acquires absorption signal from the detection mechanism.

Sample

The disclosed sensor detects gases dissolved in a sample liquid. The sampled liquid, commonly referred to as a sample, may be in any suitable format. In some embodiments, the degasser 1 is placed into a liquid or a body of water. In some embodiments the sensor 0 attaches to a sample jar or bottle 5 containing the liquid. In still other embodiments, the degasser, or a portion of the degasser is injected into a patient's body (e.g., into a vein).

Different embodiments of the disclosed apparatus may be adapted or well suited to detect gases within different liquids. It is within the scope of the present disclosure for the liquid to be practically any liquid, including but not limited to, fresh water, salt water, wastewater, oil, processing liquids, beverages, body fluids, blood, urine, mixtures thereof, and the like.

Target Analytes

The present disclosure provides a system and method for detecting an analyte dissolved in a liquid. Different embodiments of the present invention may be configured to detect different analytes. In some cases, changes to the physical properties of various components will be required to detect a different analyte. A non-limiting example of analytes for detection include $CO_2$, $pCO_2$ (partial pressure of $CO_2$), $CH_4$, $C_2H_2$, $SO_2$, $SO_3$, $H_2S$, $O_2$, $CO$, $pO_2$, aromatic gases, noble gases, acetone and other organic molecules, and the like.

Housings

Figure 10:
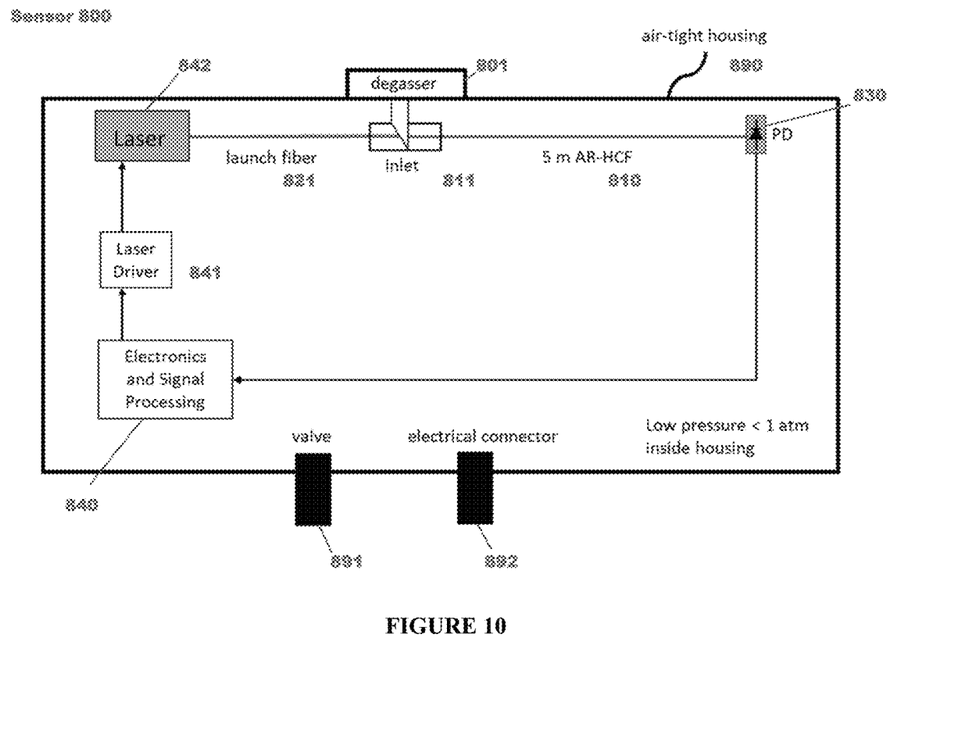
FIG. 10 illustrates an embodiment of the present invention wherein the components are housed within a substantially waterproof housing.

In some embodiments, the apparatus disclosed herein is adapted to operate in wet or submerged environments. An appropriate housing is provided to facilitate these uses. In some embodiments, such as Sensor 800 depicted in FIG. 10, a housing 890 surrounds the sensor apparatus to protect from water, other liquids, and corrosion. These housings are commonly known in the art as water resistant housings. In some embodiments, a water-tight housing surrounds the sensor apparatus, such that the sensor may be fully immersed into a liquid. These housings are commonly known as waterproof housings. Embodiments with housings are constructed such that housing forms at least one opening for the degasser 801. The components are configured such that the opening along with the degasser form a liquid tight seal to prevent water or other liquids from entering the interior of the housing, while still enabling the degasser to be in contact with the surrounding liquid. In embodiments with a propagator and a housing, a valve 891 may be provided to allow the propagator to remove waste gas from the apparatus and the housing without allowing ingress of any liquids. Likewise, power may either be provided by on-board power supply (such as a battery) or otherwise an electrical connector 892 may be provided to allow use of external power. In one or more embodiments, the sensor may be transported within the housing.

Method of Use

Figure 8:
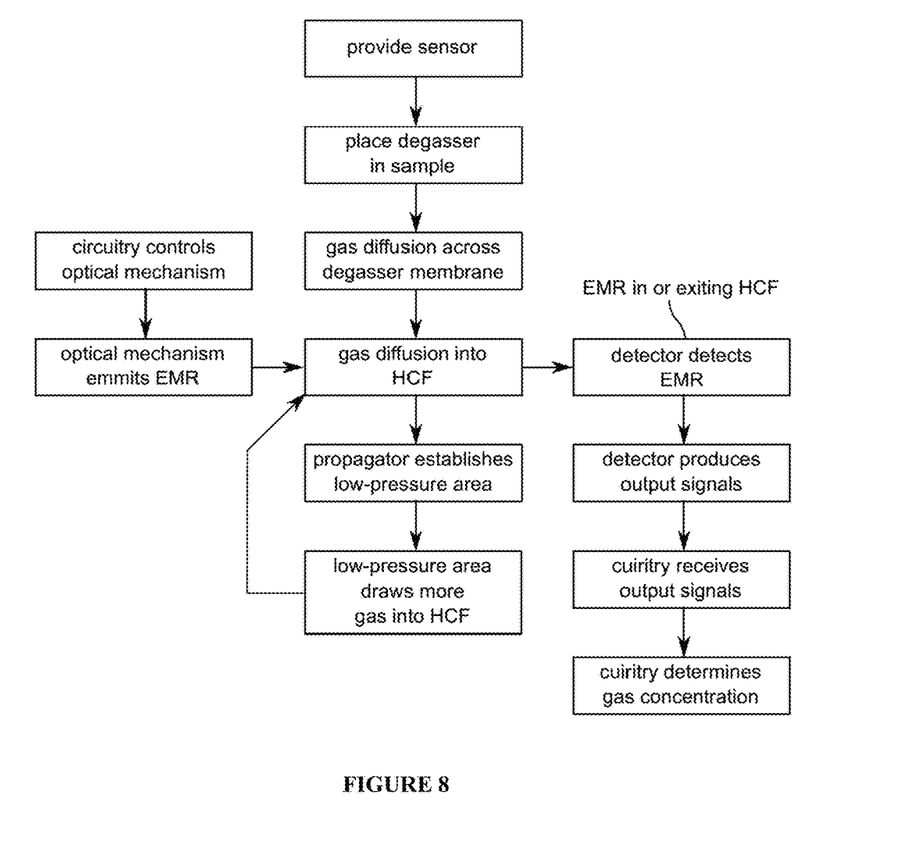
FIG. 8 illustrates one method of use of an embodiment according to the present invention.

Presently herein several exemplary methods of use of several embodiments will be discussed. One embodiment and method of use thereof is illustrated in the flow-diagram set forth in FIG. 8. As shown, a sensor apparatus is provided to detect one or more gases dissolved in a liquid. The sensor apparatus comprises a degasser 1, an optical mechanism 20, a HCF 10, a propagator 60, a detector 32, and circuitry 40 as described elsewhere herein (numbers provided for ease of reference to the figures of the sensors provided, although components are not depicted in the flow chart). The degasser is placed into a liquid that comprises at least one dissolved gas, and the gas dissolved within that liquid diffuses into the HCF's interior. The apparatus is controlled, typically by the circuitry, to emit from the optical mechanism electromagnetic radiation (EMR) into the HCF's interior. The detector 32 is configured to detect the electromagnetic radiation inside the HCF's interior. Gas diffuses into the degasser 1 from the liquid and into the HCF's interior. Electromagnetic radiation is emitted from the optical mechanism 20 and directed into the HCF's interior. The detector 32 detects the amount of electromagnetic radiation originating from the HCF's interior. Here the term "originating" encompasses EMR within and exiting (i.e., having traveled through at least once the HCF). Often the detector 32 detects the absorption of the EMR and produces an output signal which it sends to the circuitry 40. The circuitry and it associated software may calculate the amount of a gas based on the output signal and the known amount of input electromagnetic radiation emitted into the HCF's interior (i.e., an input signal).

In some methods, the propagator 60 establishes a low-pressure area. The low-pressure area is often at the end of the HCF farthest away from the degasser 1. In some cases, the apparatus further has a gas-tight detection chamber 31 to which the propagator 60 is attached and in which the detector 32 resides. In these cases, the method of use further includes the establishment of a low-pressure area in the detection chamber. In some cases, the optical mechanism 20 is also located within the detection chamber; in these cases, the detection chamber 31 is connected to one end of the HCF 10, while the second end of the HCF 10 is connected to an inlet 11 connected to the degasser 1. A mirror 33 is often within the inlet 11 such that when the electromagnetic radiation is emitted from the optical mechanism 20, the EMR enters the HCF's interior at the first HCF end, exits the HCF at the second end, and reflects off the mirror. The EMR then reenters the HCF's second end, passes through the HCF, exits the HCF's first end, and is received by the detector (see FIG. 1C provides an example of the EMR movement as outlined above). Often in these cases, a prism 34 or similar mechanism enables the delivery of the electromagnetic radiation (i) from the optical mechanism 20 to the HCF's first end as well as (ii) from the HCF's first end (after traveling through the HCF twice and reflecting off the mirror) to the detector. In some embodiments with a propagator and mirror, such as sensor 300 illustrated in FIG. 9B, both ends of the HCF terminate into gas-tight housings; the mirror 333 is at one HCF 310 end within the inlet 311, and the opposite HCF end terminates in a gas-tight housing to which the propagator 360 may also be connected. In some of these embodiments, the propagator is further connected to the degasser end not attached to the inlet. In other of these embodiments, the degasser is connected to the second gas-tight housing and the propagator is connected to the inlet, the degasser is optionally also connected to the propagator to enable gas circulation.

In some uses, the liquid is first placed into a sample container 5, which may be any suitable containment vessel as known in the art. In some uses, the sample container 5 is secured to the apparatus such that it is gas-tight to the apparatus, preventing any gas leakage from the liquid. In some uses, the liquid is part of a larger body of liquid (e.g., a stream, the ocean, etc.). In some uses, the liquid is a body fluid. In some uses, the degasser is inserted into the body of a patient to sample dissolved gasses within the patient's body. In some of these uses, the degasser is inserted into the urinary tract. In other of these uses, the degasser is attached to a needle and introducer sheath, the needle is inserted into a patient's body (often in a vein or artery) and the introducer sheath is slid through the needle and into the patient's body. The degasser is then slid through the introducer sheath and into the patient's body, where gas diffusion may occur from the body fluid liquid and into the degasser's interior. Catherization and methods of use are well known in the art and are described in more detail in U.S. Pat. Nos. 5,674,232 A and 10,595,820 B2, both incorporated by reference in their entirety herein.

In one use, the liquid to be tested is placed into a sample jar or introduced into a sample container as commonly known, and the degasser is located within the sample jar. In another use, the degasser is placed into a liquid for which a gas is dissolved therein.

Example

Presently, a specific example of one embodiment of the present disclosure will be presented in detail. In this exemplary embodiment, we present a hollow core fiber (HCF) optic sensor capable of measuring dissolved gas in liquids using microscopic sample gas sizes (only 40 nanoliters of sample gas). We utilize a revolver-type AR-HCF 10 and 2$f$ WMS to realize a simple and compact sensor for measuring dissolved gases in fluids (FIG. 1A). For gas extraction, the sensor apparatus employs a novel gas-permeable polymer membrane degasser, the small size of which is only feasible due to the tiny amount of gas required to fill the HCF, and we demonstrate and characterize the sensor's performance for measuring the analyte of dissolved methane in water, showing that this sensor is simple, robust, and compact. Dissolved methane in water represents only one possible detectable gas in one possible liquid; other gasses and liquids are within the scope of this invention. We demonstrate the sensing technique using wavelength modulation spectroscopy for measuring methane dissolved in water and achieve a lower detection limit of less than 300 ppb with a response time of 8.1 minutes.

In this embodiment, the optical mechanism is a 1650.9 nm distributed feedback (DFB) laser (15 mW LD-PD/Ideal Photonics) coupled to a HCF by an optical fiber (here a laser fiber) and an inlet mechanism. The HCF comprises a 5 meter AR-HCF, commercially available from iXblue, catalog number IXF-ARF-45-240, with an operating wavelength at 1550 nm. The inlet mechanism comprises a FC/APC (ceramic ferrules/angled physical contact) connector for the laser fiber and an FC/PC (ceramic ferrules/physical contact) connector for the AR-HCF. This configuration leaves a small ~85 µm gap between the two fibers (laser fiber and AR-HCF) through which gas can enter the HCF. The fiber connection is enclosed in the inlet's housing, here a custom fabricated and sealed "tee" adapter that interfaces to a gas-permeable polymer degasser. The degasser is sealed at its distal end to prevent liquid (e.g., water) from entering. Care was taken in the design to minimize the gas volume inside the inlet mechanism. Light at the opposite end of the AR-HCF exits into a detection chamber containing the detection mechanism, here a photodiode used to measure absorption signal. The detection chamber is gas-tight (i.e., sealed) and is connected to a vacuum pump which is used to create a pressure differential between the inlet and outlet of the hollow core fiber (i.e., first and second HCF ends). Such a pressure gradient facilitates rapid filling of the HCF.

As discussed above, different types of fibers may be used for the HCF. In the currently preferred embodiment, the AR-HCF was chosen for its nearly single-mode operation in the near-infrared, where fiber-coupled laser and detector components are both inexpensive and widespread, and for the HCF's 46 µm core diameter, which results in a small sample volume that can still be filled within minutes. The operating range of the AR-HCF is 1350 nm to 1850 nm, which covers a range of important gases including $CH_4$, $CO_2$, CO, $C_2H_2$, $H_2S$, HCl, $NH_3$, and NO. Other fibers will have different properties and enable the apparatus, in other embodiments, to measure different gases.

In this embodiment, the AR-HCF structure consists of the 46 µm core surrounded by a 99 µm OD cladding composed of seven tubes each approximately 12 µm in diameter. The detector is an amplified Indium-Gallium-Arsenide (InGaAs) photodiode. The optical mechanism (here a laser) was centered on the 1650.96 nm methane absorption transition via current and temperature tuning using a laser driver, commercially available from Thorlabs, catalog number ITC4001.

In this embodiment, the circuitry comprises a lock-in amplifier and an optical driver. The lock-in amplifier (commercially available from Zurich Instruments HLF2LI) is connected to the optical mechanism, the optical driver, and the detector. The lock-in amplifier was used to both generate a small amplitude 5 kHz sine wave laser current modulation signal and to acquire the 2f WMS absorption signal. The amplitude of the current modulation waveform was adjusted to maximize the magnitude of the 2f signal.

In this embodiment, the degasser comprises a Teflon AF polymer degasser (508 µm OD×254 µm ID×1 m long) that was used to extract the dissolved gas. This length was long enough to ensure the gas inside the degasser inlet was in close equilibrium with the surrounding liquid (here water) before entering the AR-HCF. While, in some embodiments such equilibrium is not required for a dissolved gas sensor, in this embodiment, close equilibrium with the liquid makes sensor calibration and characterization much simpler since it significantly reduces the effect of the membrane's selectivity to various gases.

Figure 2:
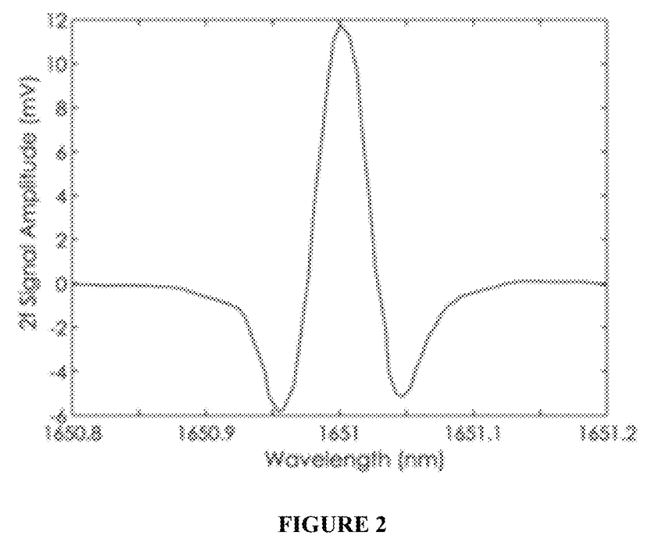
FIG. 2 illustrates an absorption feature recorded by the detector while scanning the optical mechanism's center wavelength across an analyte transition line (here the 1650.96 methane transition at a methane concentration of 100 ppm).

To first characterize the sensor's response to methane gas, the sensor was put into gas-calibration mode, illustrated in FIG. 1B, where the degasser is removed from the inlet, leaving only a small stem that was inserted into the sample container filled with a 100 ppm methane/air mixture. Once the signal had stabilized, a 10 Hz triangle waveform was added to the laser modulation to scan the laser's center wavelength and observe the 2f signal for the full absorption feature, as illustrated in FIG. 2.

Next, the 10 Hz scan was turned off, and the center wavelength of the laser was passively held (i.e., with no feedback) at 1650.96 nm for the remainder of the experiments. The sensor's response to methane gas was then calibrated by replacing the gas in the sample container with pure nitrogen gas followed by increasing concentrations of methane/air mixtures in steps from 10 ppm to 10,000 ppm. The gas in the sample container was held at atmospheric pressure (i.e., 1 atm). The 2f signal recorded during the calibration is illustrated as the dark black line in FIG. 3.

Figure 4:
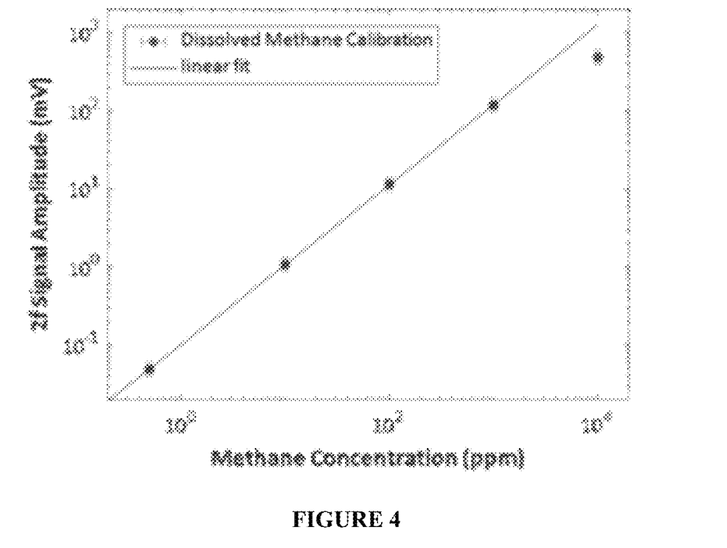
FIG. 4 illustrates a calibration of the exemplified embodiment during calibration for measuring dissolved methane through the membrane inlet. The linear fit was performed using only the first four points since weak absorption is no longer true at 10,000 ppm.

A dissolved calibration using dissolved gases was then performed by re-assembling the Teflon degasser tube into the inlet and inserting it into the sample container. The sample container was then filled with tap water which was sparged with pure nitrogen followed by sparging increasing concentrations of methane/air mixtures until equilibrium was reached. During the full experiment, the solution was continuously stirred to avoid diffusion boundary layer effects on the water side of the degasser membrane. The 2f signal during the calibration is shown by the blue data in FIGS. 3 and 4. The similarity between the two calibrations in FIG. 3 suggests the gas is well equilibrated inside the degasser inlet before entering the hollow core fiber HCF, and that the degasser has minimal impact on the sensor's ability to accurately quantify methane.

Figure 5:
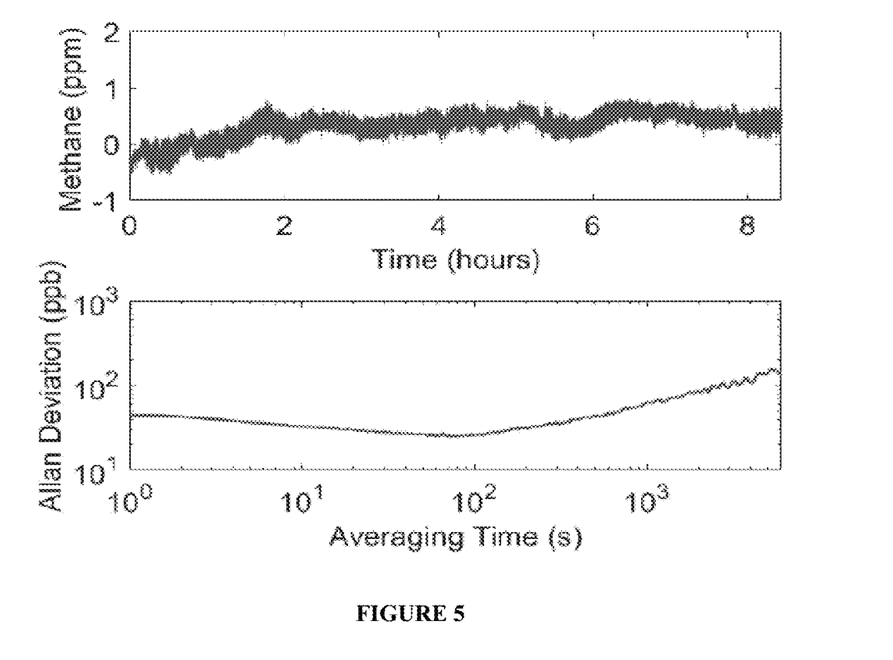
FIG. 5 illustrates one embodiment's response during a stability test over 8 hours.
Figure 6:
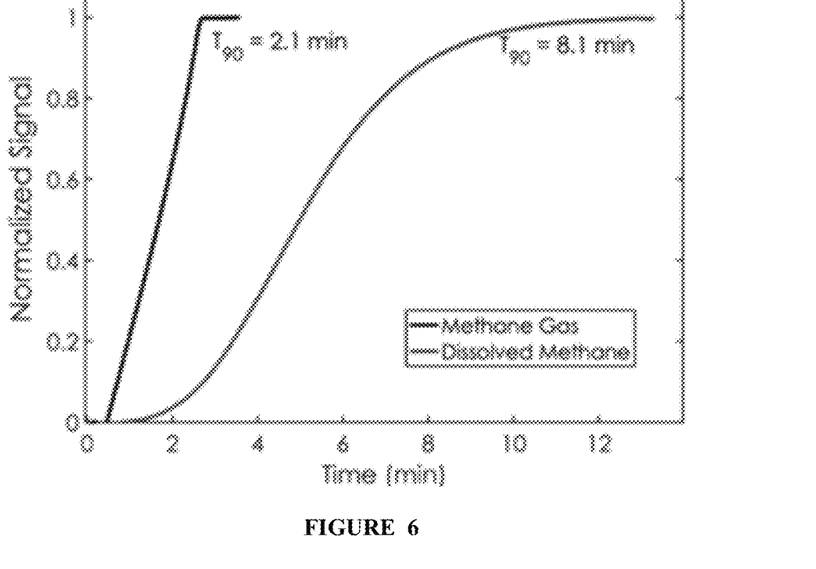
FIG. 6 illustrates the response time of the sensor according to the exemplified embodiment to a 1,000 ppm step of methane gas sent directly into the AR-HCF (dark color) and for measuring dissolved methane through the membrane inlet (light color).

As illustrated in FIG. 5, The sensor's detection limit was assessed by equilibrating the sample water with zero air and monitoring the signal over a period of 8 hours (FIG. 6). An Allan deviation analysis was used to determine the performance over various time scales. The result agrees well with the performance described above in that changes below 100 ppb are resolvable over time scales of seconds to minutes, reaching a minimum of 25 ppb for an averaging time of ~100 s. However, long-term drift becomes the predominant feature affecting performance for time scales longer than ten minutes, and it reaches 6=230 ppb over several hours, which was defined to be the sensor's lower detection limit.

For a final test, the response time of the sensor was characterized by recording the signal when it was immediately subjected to a 1,000 ppm step in methane in either gaseous or dissolved form (FIG. 6). The response to a gas phase sample (i.e., not a fluid sample) was tested similarly as described above in that the degasser inlet was removed and the gas in the sample container was quickly flushed with a 1,000 ppm methane/air mixture. For methane dissolved in fluid, the step response was achieved by filling the sample container with water, pre-equilibrating the water with 1,000 ppm methane, and quickly inserting the degasser inlet into the solution. The results show that the T90 (time to reach 90% of signal) response time for the gas phase test is 2.1 minutes (FIG. 6, dark line), while the T90 response time for the dissolved gas test is 8.1 minutes (FIG. 6, light line). The shape of the two curves is also quite different due to the different processes limiting the response time. The gas phase test exhibits sharp start and end points, indicative of the sample gas immediately reaching and then filling the HCF. In contrast, the dissolved phase test exhibits a more gradual response which is dominated by the gas concentration reaching equilibrium inside the degasser.

Overall, the data generated by this embodiment demonstrates the use of hollow core fibers to measure dissolved gas in liquids with a response time of minutes. The small gas volume required to fill the HCF also enables the use of a polymer degasser membrane to extract gas from the fluid (i.e., liquid) for analysis. The hollow core fiber and degasser used could be applicable to a range of applications. For example, the degasser can withstand pressures >1,000 psi without collapsing, which enables possibilities for measuring environmental gases in the deep ocean or gases in high pressure industrial fluids. The small diameter of the degasser also enables dissolved gas analysis inside small tubes or when only a limited amount of sample is available for analysis. Such situations might occur in microfluidic systems or when analyzing samples of blood or saliva. While the detection limit and response time as reported offer suitable performance for many situations, in the future, both can be tailored to various applications by adjusting the properties of the degasser or the hollow core fiber. For example, some of the embodiments disclosed herein were designed for high pressure ocean applications, and thus used a thick-walled durable material for the degasser. Consequently, the degasser length could be reduced for low pressure applications by selecting a different material or wall thickness, or by relaxing the requirement for gas equilibration. By varying these parameters, along with the length of the hollow core fiber, one could increase or decrease sensitivity and response time, with various compromises between the two. Therefore, a wide variety of sensor configurations are possible for many conceivable applications.

Although specific features of the present invention are shown in some drawings and not in others, this is for convenience only, as each feature may be combined with any or all the other features in accordance with the invention. While there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature.

It is the intention, therefore, to be limited only as indicated by the scope of the claims appended hereto. Other embodiments will occur to those skilled in the art and are within the following claims.

The invention claimed is:

1. A method of detecting a gas dissolved in a liquid, comprising the steps of:
   (a) providing an apparatus comprising:
      a degasser;
      an optical-based solution for analyte analysis or a laser-based solution for analyte analysis configured to produce electromagnetic radiation;
      a hollow core fiber HCF having a first end, a second end, and a hollow interior, gaseously connected to said degasser and configured to accept gas and electromagnetic radiation into said HCF's interior;
      a detector configured to detect electromagnetic radiation in and/or exiting said HCF's interior;
      a propagator configured to establish a low-pressure area in the proximity of said HCF's first end and a detection chamber connected to said propagator and said HCF;
      an inlet, wherein the inlet connected to the degasser and the HCF;
      a mirror, wherein the mirror is located within said inlet and configured to reflect said electromagnetic radiation; and wherein said detector is located within said detection chamber;
      a prism within said detection chamber configured to direct electromagnetic radiation from said optical-based solution for analyte analysis or a laser-based solution for analyte analysis into said HCF's interior and direct electromagnetic radiation from said HCF's interior to said detector;
      and circuitry connected to said optical-based solution for analyte analysis or a laser-based solution for analyte analysis and said detector;
   (b) placing said degasser into or in fluid communication with a liquid comprising a dissolved gas;
   (c) diffusing gas from said liquid into said HCF's interior;
   (d) emitting electromagnetic radiation from said optical mechanism into said HCF's interior by said prism;
   (e) detecting said electromagnetic radiation with said detector;
   (f) establishing an area of low-pressure with said propagator;
   (g) producing output signals corresponding to said electromagnetic radiation detection by the detector;
   (h) sending said output signals to said circuitry; and
   (i) reflecting said electromagnetic radiation exiting said HCF with said mirror back into said HCF.

2. The method of claim 1 further comprising the step of (i) controlling said optical-based solution for analyte analysis or a laser-based solution for analyte analysis with said circuitry.

3. The method of claim 1 wherein said liquid is selected from a sample located within a sample container or a larger body of liquid.

4. The method of claim 1 further comprising the step of (k) inserting said degasser into a patient's body.

5. The method of claim 1 further comprising the steps of:
   (l) attaching a needle and introducer sheath to said degasser;
   (m) inserting said needle into a patient's body; and
   (n) moving said introducer sheath into said patient's body.

6. The method of claim 5, wherein said steps (l) through (n) are performed before the step of (o) inserting said degasser into said patient's body.

7. The method of claim 6 further comprising the steps of:
   (p) placing said apparatus into a submersible housing comprising an opening;
   (q) placing said degasser through said opening, wherein said degasser, said opening, and said submersible housing form a liquid-tight seal; and
   (r) placing said submersible housing into said liquid.

* * * * *